(12) United States Patent
Pastore et al.

(10) Patent No.: US 7,621,906 B2
(45) Date of Patent: Nov. 24, 2009

(54) METHOD AND APPARATUS TO DELIVER DRUG AND PACING THERAPY FOR TREATMENT OF CARDIAC DISORDERS

(75) Inventors: Joseph M. Pastore, Oakdale, MN (US); Jeffrey Ross, Roseville, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 414 days.

(21) Appl. No.: 10/925,508

(22) Filed: Aug. 25, 2004

(65) Prior Publication Data

US 2006/0047318 A1    Mar. 2, 2006

(51) Int. Cl.
*A61K 9/22* (2006.01)
(52) U.S. Cl. .................. 604/891.1; 604/890.1; 604/20; 607/120
(58) Field of Classification Search ............. 604/890.1, 604/891.1, 19, 20, 21; 607/120
See application file for complete search history.

(56) References Cited

U.S. PATENT DOCUMENTS

| | | | |
|---|---|---|---|
| 5,347,241 A | 9/1994 | Panaretos et al. | |
| 5,354,264 A | 10/1994 | Bae et al. | |
| 5,558,632 A | 9/1996 | Lloyd et al. | |
| 5,733,313 A | 3/1998 | Barreras, Sr. et al. | |
| 5,807,306 A | 9/1998 | Shapland et al. | |
| 5,865,787 A * | 2/1999 | Shapland et al. | 604/21 |
| 6,117,296 A | 9/2000 | Thomson | |
| 6,184,030 B1 | 2/2001 | Katoot et al. | |
| 6,185,461 B1 | 2/2001 | Er | |
| 6,388,043 B1 | 5/2002 | Langer et al. | |
| 6,571,125 B2 * | 5/2003 | Thompson | 604/20 |
| 6,689,117 B2 | 2/2004 | Sweeney et al. | |
| 6,693,133 B1 | 2/2004 | Lopaschuk et al. | |
| 6,802,811 B1 | 10/2004 | Slepian | |
| 6,824,561 B2 * | 11/2004 | Soykan et al. | 623/1.42 |
| 6,969,382 B2 * | 11/2005 | Richter | 604/890.1 |
| 6,976,982 B2 * | 12/2005 | Santini et al. | 604/891.1 |
| 2002/0035346 A1 * | 3/2002 | Reynolds et al. | 604/20 |

(Continued)

FOREIGN PATENT DOCUMENTS

WO    WO-98/02150    1/1998

OTHER PUBLICATIONS

Elisseeff, Jennifer, et al., "Controlled-release of IGF-I and TGF-B1 in a photopolymerizing Hydrogel for cartilage tissue engineering", *Journal of Orthopaedic Research*, vol. 19, (2001),1098-1104.

(Continued)

*Primary Examiner*—Kevin C Sirmons
*Assistant Examiner*—Bhisma Mehta
(74) *Attorney, Agent, or Firm*—Schwegman, Lundberg & Woessner, P.A.

(57) ABSTRACT

A drug delivery system uses an electrically sensitive polymer to store a drug and applies an electric field onto the electrically sensitive polymer for quantitatively and temporally controlled drug delivery. In one embodiment, the drug delivery system is part of a cardiac rhythm management (CRM) system that includes an implantable CRM device and an implantable drug delivery device. The implantable CRM device delivers electrical therapies to a heart and controls the implantable drug delivery device by producing the electrical field with controllable amplitude, frequency, and timing.

19 Claims, 7 Drawing Sheets

U.S. PATENT DOCUMENTS

| | | | |
|---|---|---|---|
| 2003/0138415 | A1 | 7/2003 | Shepard |
| 2003/1014942 | * | 8/2003 | Richter .................. 604/500 |
| 2004/0138648 | A1 | 7/2004 | Sweeny et al. |
| 2004/0230274 | A1 | 11/2004 | Heil et al. |
| 2005/0043675 | A1 | 2/2005 | Pastore et al. |
| 2005/0137626 | A1 | 6/2005 | Pastore et al. |
| 2005/0192637 | A1 | 9/2005 | Girouard et al. |
| 2005/0288721 | A1 | 12/2005 | Girouard et al. |
| 2006/0015146 | A1 | 1/2006 | Girouard et al. |

OTHER PUBLICATIONS

"U.S. Appl. No. 10/890,825 Final Office Action mailed Jun. 7, 2007", 10 pgs.

"U.S. Appl. No. 10/890,825 Non Final Office Action mailed Jan. 11, 2007", 8 pgs.

"U.S. Appl. No. 10/890,825 Response filed Apr. 11, 2007 to Non Final Office Action mailed Jan. 11, 2007", 17 pgs.

"U.S. Appl. No. 10/890,825 Response filed Sep. 7, 2007 to Final Office Action mailed Jun. 7, 2007", 22 pgs.

"U.S. Appl. No. 10/890,825, Response filed Feb. 20, 2008 to Non-Final Office Action mailed Nov. 20, 2007", 20 pgs.

"U.S. Appl. No. 10/890,825, Non-Final Office Action mailed Nov. 20, 2007", 10 pgs.

"U.S. Appl. No. 10/890,825, Response filed Aug. 11, 2008 to Non Final Office Action mailed May 13, 2008", 18 pgs.

"U.S. Appl. No. 10/890,825, Non-Final Office Action mailed May 13, 2008", 10 pgs.

"U.S. Appl. No. 10/890,825, Non-Final Office Action mailed Nov. 14, 2008", 12 pgs.

"U.S. Appl. No. 10/890,825, Response filed Feb. 23, 2009 to Non Final Office Action mailed Nov. 14, 2008", 22 pgs.

* cited by examiner

METHOD AND APPARATUS TO DELIVER DRUG AND PACING THERAPY FOR TREATMENT OF CARDIAC DISORDERS

CROSS-REFERENCE TO RELATED APPLICATION

This application is related to co-pending, commonly assigned U.S. patent application Ser. No. 10/890,825, entitled "METHOD AND APPARATUS FOR CONTROLLED GENE OR PROTEIN DELIVERY," filed on Jul. 14, 2004, U.S. patent application Ser. No. 10/862,716, entitled "METHOD AND APPARATUS TO MODULATE CELLULAR REGENERATION POST MYOCARDIAL INFARCT," filed on Jun. 7, 2004, U.S. patent application Ser. No. 10/788,906, entitled "METHOD AND APPARATUS FOR DEVICE CONTROLLED GENE EXPRESSION," filed on Feb. 27, 2004, U.S. patent application Ser. No. 10/742,574, entitled "DRUG DELIVERY SYSTEM AND METHOD EMPLOYING EXTERNAL DRUG DELIVERY DEVICE IN CONJUNCTION WITH COMPUTER NETWORK," filed on Dec. 19, 2003, U.S. patent application Ser. No. 10/645,823, entitled "METHOD AND APPARATUS FOR MODULATING CELLULAR METABOLISM DURING POST-ISCHEMIA OR HEART FAILURE," filed on Aug. 21, 2003, and U.S. patent application Ser. No. 09/740,129, entitled "DRUG DELIVERY SYSTEM FOR IMPLANTABLE MEDICAL DEVICE," filed on Dec. 18, 2000, now issued as U.S. Pat. No. 6,689,117 which are hereby incorporated by reference in their entirety.

TECHNICAL FIELD

This document generally relates to drug delivery systems and particularly, but not by way of limitation, to drug delivery devices each being part of a cardiac rhythm management (CRM) system providing for electrical and drug therapies.

BACKGROUND

Drug delivery systems are each used to deliver a drug to a specific target region in a person's body to treat a condition in or related to that region in a localized and efficient manner. One example of such a target region includes a portion of the person's circulatory system, including the heart or a portion of the heart.

The heart is the center of a person's circulatory system. It includes an electro-mechanical system performing two major pumping functions. The left portions of the heart draw oxygenated blood from the lungs and pump it to the organs of the body to provide the organs with their metabolic needs for oxygen. The right portions of the heart draw deoxygenated blood from the organs and pump it into the lungs where the blood gets oxygenated. The pumping functions are accomplished by contractions of the myocardium (heart muscles). In a normal heart, the sinoatrial node, the heart's natural pacemaker, generates electrical impulses, known as action potentials, that propagate through an electrical conduction system to various regions of the heart to excite myocardial tissues in these regions. Coordinated delays in the propagations of the action potentials in a normal electrical conduction system cause the various regions of the heart to contract in synchrony such that the pumping functions are performed efficiently.

A blocked or otherwise damaged electrical conduction system causes the myocardium to contract at a rhythm that is too slow, too fast, and/or irregular. Such an abnormal rhythm is generally known as arrhythmia. Arrhythmia reduces the heart's pumping efficiency and hence, diminishes the blood flow to the body. A deteriorated myocardium has decreased contractility, also resulting in diminished blood flow. A heart failure patient usually suffers from both a damaged electrical conduction system and a deteriorated myocardium. The diminished blood flow results in insufficient blood supply to various body organs, preventing these organs to function properly and causing various symptoms.

Various drugs are available to treat such cardiac disorders. Some drugs are most effective when directly applied to the heart, such as to a cardiac region where a disorder originates. Electrical therapies delivered to the heart, such as pacing and defibrillation therapies, have been developed and applied to treat various cardiac disorders including arrhythmia and heart failure. When properly combined, drug and electrical therapies benefit a patient to an extent beyond what is achievable by either drug therapy or electrical therapy alone. Thus, there is a need for a system that efficiently delivers coordinated drug and electrical therapies.

SUMMARY

A drug delivery system uses an electrically sensitive polymer to store a drug and applies an electric field onto the electrically sensitive polymer for quantitatively and temporally controlled drug delivery. The electrically sensitive polymer has an electrically controllable structure being a function of an electric field applied on the electrically sensitive polymer.

In one embodiment, a system includes an implantable drug delivery device and an implantable lead connected to the implantable drug delivery device. The implantable drug delivery device includes a drug storage device. At least a portion of the drug storage device is made of the electrically sensitive polymer. One or more electrodes are connected to the drug storage device to apply the electric field on the electrically sensitive polymer. The implantable lead has one end connected to the implantable drug delivery device and another end with a lead connector. One or more conductors extend within the lead and provide electrical connection between the lead connector and the one or more electrodes.

In one embodiment, a drug delivery device includes a storage compartment having a chamber. At least a portion of the wall forming the chamber is made of the electrically sensitive polymer.

In one embodiment, an apparatus for treating a heart includes an implantable lead coated with a drug delivery polymer. The implantable lead includes one or more electrodes to provide electrical connection to the heart. A material including the electrically sensitive polymer is coated on at least a portion of the implantable lead. A drug is embedded in that material.

In one embodiment, a bulking agent used to bulk at least a portion of a myocardium includes the electrically sensitive polymer. A drug embedded in the electrically sensitive polymer.

In one embodiment, an electric field is applied to the electrically sensitive polymer containing a drug to control the release of the drug. In one embodiment, a plurality of electrical signals are delivered to the electrically sensitive polymer. The electrical signals each control an electric field strength in a portion of the electrically sensitive polymer. This allows control of a spatial distribution of electric field strength in the electrically sensitive polymer.

In one embodiment, a release of a drug embedded in a bulking agent made of a material including at least the electrically sensitive polymer is controlled by applying an electrical field to the bulking agent. The bulking agent is implanted in the myocardium.

This Summary is an overview of some of the teachings of the present application and not intended to be an exclusive or exhaustive treatment of the present subject matter. Further details about the present subject matter are found in the detailed description and appended claims. Other aspects of the invention will be apparent to persons skilled in the art upon reading and understanding the following detailed description and viewing the drawings that form a part thereof, each of which are not to be taken in a limiting sense. The scope of the present invention is defined by the appended claims and their equivalents.

BRIEF DESCRIPTION OF THE DRAWINGS

In the drawings, which are not necessarily drawn to scale, like numerals describe similar components throughout the several views. The drawings illustrate generally, by way of example, but not by way of limitation, various embodiments discussed in the present document.

DETAILED DESCRIPTION

Figure 1:
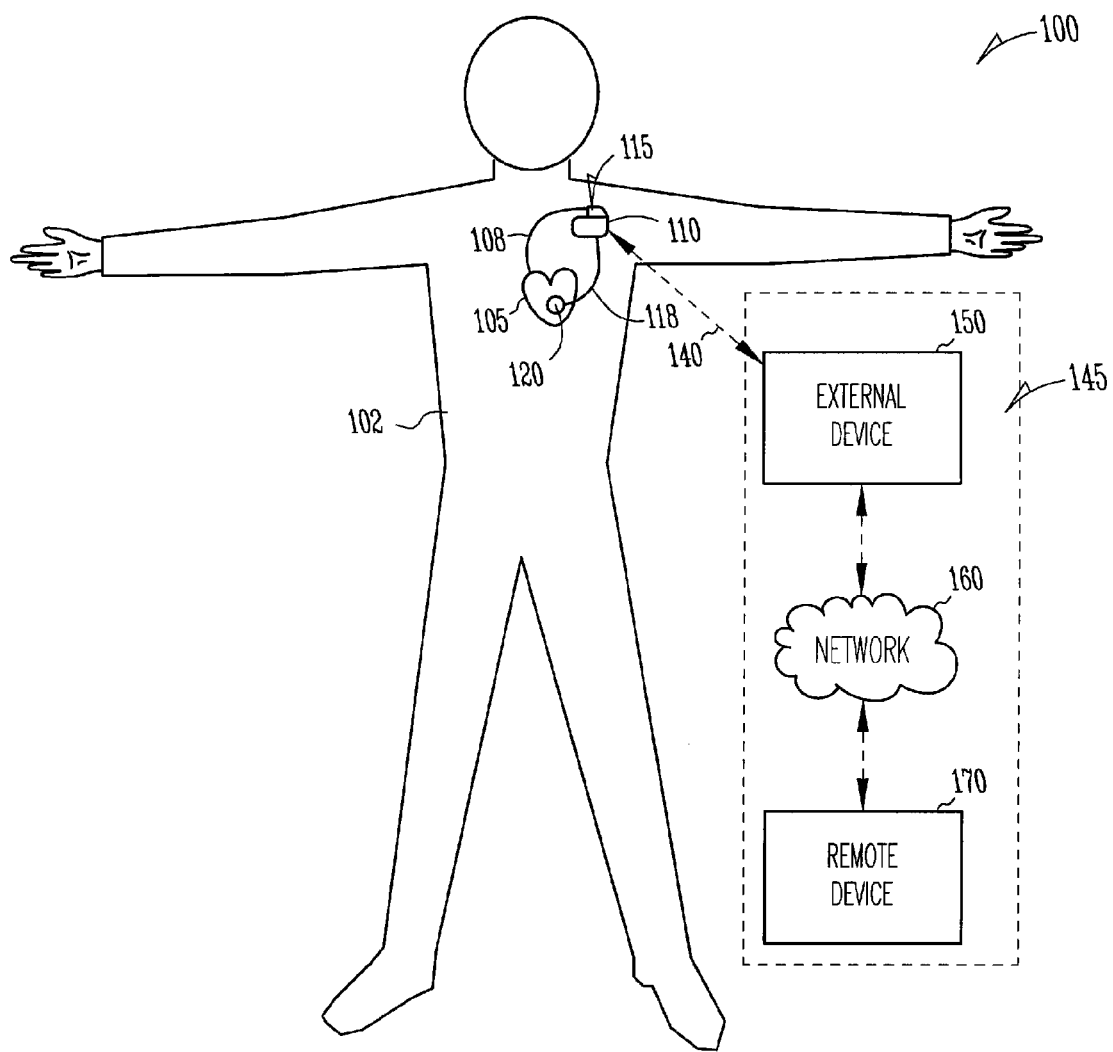
FIG. 1 is an illustration of an embodiment of a CRM system including an implantable drug delivery device and portions of an environment in which the CRM system is used.

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that the embodiments may be combined, or that other embodiments may be utilized and that structural, logical and electrical changes may be made without departing from the spirit and scope of the present invention. The following detailed description provides examples, and the scope of the present invention is defined by the appended claims and their equivalents.

It should be noted that references to "an", "one", or "various" embodiments in this disclosure are not necessarily to the same embodiment, and such references contemplate more than one embodiment.

This document discusses, among other things, a drug delivering device using an electrically sensitive polymer for electrically controlled drug release. The electrically sensitive polymer has a structure that is controllable by applying an electric field onto it. A drug is embedded in a matrix made of the electrically sensitive polymer or contained in a container made of the electrically sensitive polymer. The drug is released by applying a controllable electric field to the matrix or container. While implantable drug delivery devices treating cardiac disorders are specifically described as examples, the general idea of using the electrically sensitive polymer for electrically controlled drug delivery is not limited to implantable devices or treatment of cardiac disorders. In this document, a "drug" includes one or more agents intended for use in the diagnosis, cure, mitigation, treatment, or prevention of one or more diseases. The one or more agents may be chemical, biochemical, and/or biological in nature. Such agents include, but are not limited to, one or more of an agent treating atrial tachycardia, an agent treating atrial fibrillation, an agent treating ventricular tachycardia, an agent treating ventricular fibrillation, an agent treating heart failure including its various symptoms, an agent treating diastolic dysfunction, an agent providing ischemia protection, an agent reducing fibrosis, an angiogenic agent, agent supporting a cell therapy, an agent recruiting cells for cell therapy, and an agent promoting tissue regeneration and development. Specific examples of such agents include, but are not limited to, those discussed in U.S. patent application Ser. No. 10/890,825, entitled "METHOD AND APPARATUS FOR CONTROLLED GENE OR PROTEIN DELIVERY," filed on Jul. 14, 2004, U.S. patent application Ser. No. 10/862,716, entitled "METHOD AND APPARATUS TO MODULATE CELLULAR REGENERATION POST MYOCARDIAL INFARCT," filed on Jun. 7, 2004, U.S. patent application Ser. No. 10/788,906, entitled "METHOD AND APPARATUS FOR DEVICE CONTROLLED GENE EXPRESSION," filed on Feb. 27, 2004, U.S. patent application Ser. No. 10/742,574, entitled "DRUG DELIVERY SYSTEM AND METHOD EMPLOYING EXTERNAL DRUG DELIVERY DEVICE IN CONJUNCTION WITH COMPUTER NETWORK," filed on Dec. 19, 2003, and U.S. patent application Ser. No. 10/645,823, entitled "METHOD AND APPARATUS FOR MODULATING CELLULAR METABOLISM DURING POST-ISCHEMIA OR HEART FAILURE," filed on Aug. 21, 2003, all assigned to Cardiac Pacemakers, Inc., which are hereby incorporated by reference in their entirety.

FIG. 1 is an illustration of an embodiment of a CRM system 100 and portions of an environment in which CRM system 100 is used. System 100 includes an implantable system 115 and an external system 145. Implantable system 115 includes an implantable CRM device 110, a lead system 108, and an implantable drug delivery device 120 connected to implantable CRM device 110 through a lead 118. In one embodiment, external system 145 includes an external device 150, a network 160, and a remote device 170. In another embodiment, external system 145 includes a medical device programmer. As shown in FIG. 1, implantable CRM device 110 is implanted in a body 102. Lead system 108 includes one or more pacing and/or defibrillation leads to provide electrical connections between a heart 105 and implantable CRM device 110. A telemetry link 140 provides for bidirectional communication between implantable CRM device 110 and external device 150. Network 160 provides for bidirectional communication between external device 150 and remote device 170.

The delivery of electrical and drug therapies is controlled by one or more of implantable CRM device 110, external device 150, and remote device 170. In one embodiment, implantable CRM device 110 controls the delivery of the electrical and drug therapies based on a detected signal or condition. In one embodiment, external device 150 and/or remote device 170 control the delivery of the electrical and drug therapies upon receiving the external user command. In further embodiments, external device 150 and/or remote device 170 are capable of automated controlling the delivery of the electrical and drug therapies by processing and analyzing signals and/or conditions detected by implantable CRM device 110.

Figure 2:
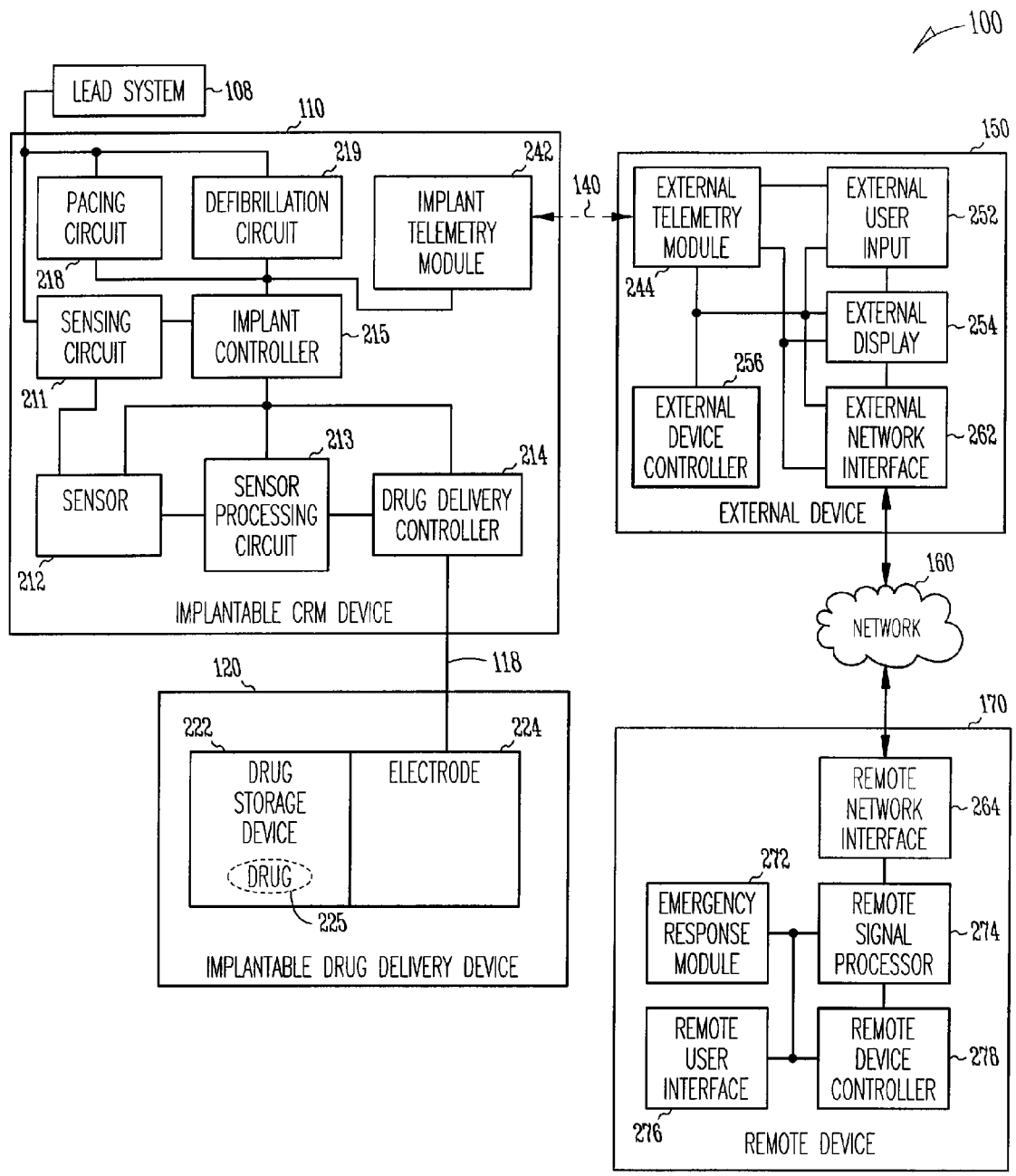
FIG. 2 is a block diagram illustrating one embodiment of the circuit of portions of the CRM system of FIG. 1.

FIG. 2 is a block diagram showing one embodiment of the circuit of portions of system 100. Implantable CRM device 110 includes a sensing circuit 211, a sensor 212, a sensor processing circuit 213, a drug delivery controller 214, an implant controller 215, a pacing circuit 218, a defibrillation circuit 219, and an implant telemetry module 242. Sensing circuit 211 senses one or more intracardiac electrograms through one or more pacing leads of lead system 108. Sensor 212 senses one or more signals used to control the delivery of the electrical and drug therapies. Sensor processing circuit 213 processes the signal sensed by sensor 212 to produce one or more parameters indicative of a need for starting, stopping, or adjusting the delivery of the electrical and/or drug therapies. Drug delivery controller 214 produces drug delivery signals based on the parameter from sensor processing circuit 213 and/or a command from implant controller 215. In one embodiment, the command includes an external user command received by a command receiver of implantable controller 215 through implant telemetry module 242 and telemetry link 140. Implant controller 215 controls the delivery of electrical therapy. In one embodiment, implant controller 215 also coordinates the delivery of electrical therapy and the delivery of drug therapy, such that system 100 delivers a coordinated electrical and drug therapy. Implant controller 215 includes a pacing controller and a defibrillation controller. The pacing controller includes a pacing algorithm execution module to control the delivery of pacing pulses by executing a pacing algorithm. In one embodiment, the pacing algorithm execution module executes a pacing algorithm designed to enhance one or more effects of the drug therapy. In one specific embodiment, the pacing algorithm execution module executes a bradycardia pacing algorithm. In another specific embodiment, the pacing algorithm execution module executes a cardiac resynchronization therapy (CRT) pacing algorithm. The CRT provides for an approximately optimal hemodynamic performance. In one embodiment, a CRT pacing algorithm is executed with one or more pacing parameters approximately optimized to maximize a measure of hemodynamic performance. In another specific embodiment, the pacing algorithm execution module executes a remodeling control therapy (RCT) pacing algorithm. The RCT alters the cardiac remodeling process, for example, by redistributing the workload and stress on the ventricular walls. In a further specific embodiment, the pacing algorithm execution module executes a dynamic pacing algorithm that dynamically adjusts pacing parameters, such as alternating between the CRT and RCT, based on a patient's changing needs and conditions. Pacing circuit 218 includes one or more pulse output channels to deliver the pacing pulses to one or more sites in heart 105 through lead system 108, with the timing and other parameters of the pacing pulses controlled by the pacing controller. Defibrillation circuit 219 includes one or more shock output channels to deliver cardioversion/defibrillation shock pulses to one or more sites in heart 105 through lead system 108, with the timing and other parameters of the shock pulses controlled by the defibrillation controller.

In one embodiment, sensor processing circuit 213 processes the signal sensed by sensor 212 before the signal is used by drug delivery controller 214 and implant controller 215 to determine whether to start, stop, or adjust the electrical and/or drug therapies. The one or more parameters produced by sensor processing circuit 213 include parameters measured and/or derived from the sensed signal. In one embodiment, sensor processing circuit 213 includes an event detector to detect one or more predetermined events indicative of a need to start, stop, or adjust the electrical and/or drug therapies. The one or more parameters produced by sensor processing circuit 213 include parameters indicative of the detection of the event and/or measured parameters associated with the detected event. In one specific embodiment, the event includes an abnormal condition. In one embodiment, sensor 212 includes a plurality of sensors to sense multiple signals used by drug delivery controller 214 and implant controller 215 to determine whether to start, stop, or adjust the electrical and/or drug therapies. Each of the multiple signals may be used by drug delivery controller 214 and/or implant controller 215 to control the drug therapy, the electrical therapy, or the coordinated electrical and drug therapies. The signal sensed by sensor 212 includes, but is not limited to, one or more of an electrogram indicative of arrhythmia and/or heart rate variability, a physiological signal indicative of ischemia, a metabolic signal indicative of a cardiac metabolic level (rate of metabolism of cardiac cells), a thoracic impedance, an intracardiac or intravascular pressure, a cardiac output or stroke volume, a neural signal indicative of activities of the autonomic nervous system, a signal indicative of renal function, a signal indicative of heart sounds, a signal indicative of respiratory sounds, a signal indicative of a strain of myocardial tissue, and a temperature signal. Examples of such signals and their use in controlling electrical and drug therapies are discussed in U.S. patent application Ser. Nos. 10/742,574, 10/788,906, 10/862,716, and 10/890,825. In one embodiment, the signal sensed by sensor 212 is used to indicate an effect of the electrical and/or drug therapies to provide a closed loop control for therapy delivery. Drug delivery controller 214 and/or implant controller 215 determine whether to start, stop, or adjust the electrical and/or drug therapies by using the signal sensed by sensor 212 as a feedback control signal. Other methods and sensors for directly or indirectly detecting an event or condition demanding the start, stop, or adjustment of the electrical and/or therapies are also usable by system 100.

Implantable CRM device 110 includes a hermetically sealed metal can to house at least portions of the electronics of the device. In one embodiment, the metal can houses at least elements 211, 213, 214, 215, 218, 219, and 242. In one embodiment, sensor 212 resides within the metal can. In another embodiment, sensor 212 is outside of the metal can. In one embodiment, sensor 212 is incorporated into lead system 108 or implantable drug delivery device 120.

Lead system 108 includes one or more pacing and/or defibrillation leads allowing sensing of electrical signals from heart 105 and delivery of pacing and/or defibrillation pulses to heart 105. In one embodiment, lead system 108 includes one or more transvenous leads each having at least one electrode disposed within heart 105. In one embodiment, lead system 108 includes one or more epicardial leads each having at least one electrode disposed on the epicardial wall of heart 105. In one embodiment, sensor 212 is built-in or attached to a lead of lead system 108.

Implantable drug delivery device 120 is connected to implantable CRM device 110 via lead 118 and includes an electrode 224 and a drug storage device 222 containing a drug 225. Drug storage device 222 includes at least a portion made of an electrically sensitive polymer having a controllable structure. The controllable structure is utilized to electrically control the release rate of a drug stored drug storage device 222. In one embodiment, the porosity of the electrically sensitive polymer is a function of an electric field applied on the electrically sensitive polymer of drug storage device 222 (i.e., the portion of drug storage device 222 made of the electrically sensitive polymer). In other words, the electrically sensitive polymer includes pores with sizes being a function of the electric field. In one embodiment, the electrically sensitive polymer enters a substantially porous state upon application of an electrical field of a predetermined amplitude and enters a substantially non-porous state upon removal of that electric field. In another embodiment, the electrically sensitive polymer enters a substantially porous state upon application of an electric field at a first amplitude and enters a substantially non-porous state upon application of the electric field at a second amplitude. In another embodiment, the binding affinity of the electrically sensitive polymer is a function of the electric field. In other words, the degree to which the drug is attracted to the electrically sensitive polymer is a function of the electric field. In one embodiment, the electrically sensitive polymer enters a state of low binding affinity upon application of an electrical field of a predetermined amplitude and enters a state of high binding affinity upon removal of that electric field. In another embodiment, the electrically sensitive polymer enters a state of low binding affinity upon application of an electric field at a first amplitude and enters a state of high binding affinity upon application of the electric field at a second amplitude. Electrode 224 is coupled to the drug storage device to apply the electric field onto the electrically sensitive polymer of drug storage device 222. In one embodiment, electrode 224 includes one electrode. In another embodiment, electrode 224 includes an electrode array having multiple electrodes. Lead 118 is an implantable lead providing for at least electrical connections between implantable drug delivery device 120 and implantable CRM device 110. In one embodiment, lead 118 including a proximal end to be connected to implantable CRM device 110 and a distal end at implantable drug delivery device 120. In one embodiment, the proximal end includes at least one lead connector to provide for a detachable connection with implantable CRM device 110, which includes at least one device connector electrically connected to drug delivery controller 214. One or more conductors extend within lead 118 from the proximal end to the distal end to provide for electrical connections between drug delivery controller and electrode 224.

In one embodiment, electrode 224 is an electrode array including a plurality of electrodes each individually controllable for applying an electrical field onto a region of the electrically sensitive polymer of drug storage device 222. In one embodiment, each electrode of the electrode array is individually controlled for producing an electric field having an individually programmed amplitude. This allows for a spatially controllable drug delivery by controlling drug release from different portions of implantable drug delivery device 120.

Implantable drug delivery device 120 is configured for implantation in a body site from which drug 225 can be released to a target organ or tissue to result in efficient, localized treatment. The size and shape of implantable drug delivery device 120 are therefore subjected to anatomical considerations and constraints. In one embodiment, implantable drug delivery device 120 includes a patch configured for epicardial attachment. In another embodiment, at least a portion of implantable drug delivery device 120 is configured for intracardiac placement. In another embodiment, at least a portion of implantable drug delivery device 120 is configured for intravascular placement.

In one embodiment, drug delivery controller 214 produces a drug delivery signal and delivers the drug delivery signal to electrode 224 through a conductor of lead 118. In a specific embodiment, drug delivery controller 214 includes an amplitude controller to produce the drug delivery signal to control the amplitude of the electric field. In another specific embodiment, drug delivery controller 214 includes a timer to produce the drug delivery signal to control the timing of application of the electric field. In another specific embodiment, drug delivery controller 214 includes a duty-cycle controller to produce the drug delivery signal to control the duty cycle of the electric field. In another embodiment, in which electrode 224 is an electrode array, drug delivery controller 214 produces a plurality of individually controllable drug delivery signals and deliver the drug delivery signals each to one or more electrodes of the electrode array through a plurality of conductors of lead 118. In a specific embodiment, drug delivery controller 214 includes an amplitude controller to produce the individually controllable drug delivery signals to result in a desirable spatial distribution of the amplitude of the electric field. In another specific embodiment, drug delivery controller 214 includes a timer to produce the individually controllable drug delivery signals to control the timing of application of the electric field to each portion of the electrically sensitive polymer of drug delivery device 222. In another specific embodiment, drug delivery controller 214 includes a duty-cycle controller to produce the individually controllable drug delivery signals to control the duty cycle of the electric field applied to each portion of the electrically sensitive polymer of drug delivery device 222.

External device 150 includes an external user input 252, an external display 254, an external device controller 256, an external telemetry module 244, and an external network interface 262. In one embodiment, external user input 252 receives an external user command controlling the electrical and/or drug therapies from a physician or other caregiver. In a further embodiment, it also receives other commands or instructions to control the operation implantable CRM device 110 including the drug delivery from implantable drug delivery device 120. In one embodiment, the external user command controlling the electrical and/or drug therapies is sent from remote device 170. External device 150 relays the external user command to implantable CRM device 110. In one specific embodiment, the external user command includes a drug delivery command. External device 150 transmits the drug delivery command to implantable CRM device 110 to result in a production of the drug delivery signal by drug delivery controller 214. External telemetry module 244 provides for a telemetry interface allowing external device 150 to communicate with implantable CRM device 110 via telemetry link 140. External network interface 262 provides for a network interface allowing external device 150 to communicate with remote device 170 via network 160.

Telemetry link 140 is a wireless bidirectional data transmission link supported by implant telemetry module 242 and external telemetry module 244. In one embodiment, telemetry link 140 is an inductive couple formed when two coils—one connected to implant telemetry module 242 and the other connected to external telemetry module 244—are placed near each other. In another embodiment, telemetry link 140 is a far-field radio-frequency telemetry link allowing implantable CRM device 110 and external device 252 to communicate over a telemetry range that is at least ten feet.

Remote device 170 includes an emergency response module 272, a remote signal processor 274, a remote user interface 276, a remote device controller 278, and a remote network interface 264. By executing one or more predetermined algorithms, remote signal processor 274 processes signals transmitted from implantable CRM device 110 and external device 150. Emergency response module 272 contacts a physician or other emergency response personnel in response to an emergency situation as detected by one of implantable CRM device 110, external device 150, and remote device 170. In one embodiment, external device 150 receives the external user command and transmits it to remote device 170 as a request for further medical attention through emergency response module 272. In another embodiment, remote signal processor 274 analyzes signals acquired by implantable CRM device 110 and transmitted to remote device 170, such as the one or more electrograms sensed by sensing circuit 211 and one or more signals sensed by sensor 212, to determine the need for starting, stopping, or adjusting the electrical and/or drug therapies. Remote user interface 276 includes a remote user input to allow a physician or other caregiver to enter the external user command from a remote location. Remote device controller 278 controls the overall operation of remote device 170. In one embodiment, remote device controller 278 generates commands controlling implantable CRM device 110 and/or external device 150 based on the received signals and the external user command. In one embodiment, remote device controller 278 executes an automatic algorithm to control the electrical and/or drug therapies, such as when the physician or other caregiver is not immediately available. Remote network interface 264 provides for an interface allowing communication between remote device 170 and external device 150 via network 160.

Network 160 provides long distance bidirectional communication between external device 150 and remote device 170. It allows management of multiple implantable systems, such as multiple units of implantable system 115 implanted in multiple patients, from a central facility at a remote location. In one embodiment, this allows prompt response by a physician or other caregiver at the central facility as demanded by the condition of a patient. In one embodiment, network 160 is based on a wireless communications system. In another embodiment, network 160 is based on a wired communications system. In one embodiment, network 160 utilizes portions of a standard communications system such as the Internet, a telephone system, or a radio frequency telemetry system. In one embodiment, one or more encryption techniques are applied for the bidirectional communication between external device 150 and remote device 170. External network interface 262 and remote network interface 264 each includes a data encryption device such that data transmitted via network 160 are encrypted.

Figure 3:
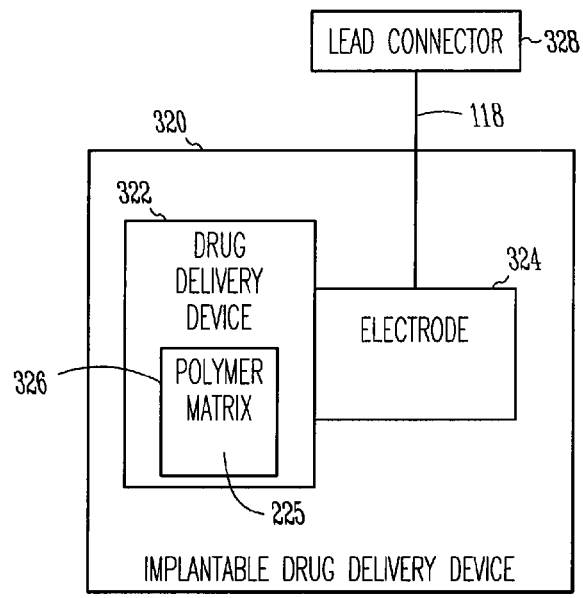
FIG. 3 is a block diagram illustrating one embodiment of the implantable drug delivery device.
Figure 4:
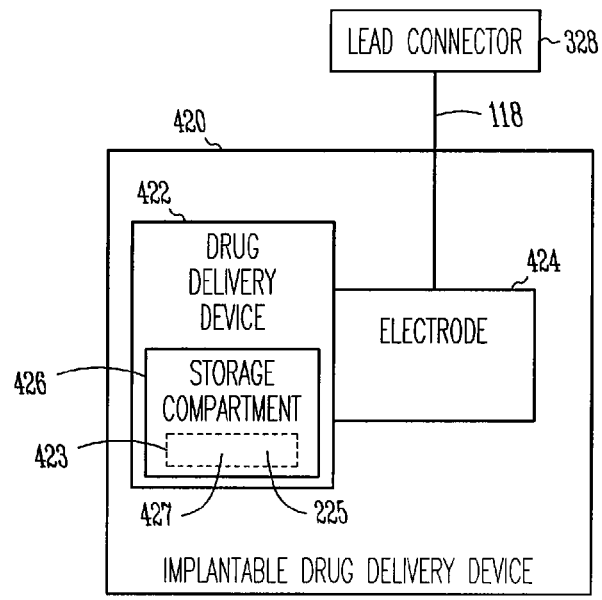
FIG. 4 is a block diagram illustrating another embodiment of the implantable drug delivery device.

FIG. 3 is a block diagram illustrating an implantable drug delivery device 320 connected to a lead connector 328 through lead 118. FIG. 4 is a block diagram illustrating an implantable drug delivery device 420 connected to lead connector 328 through lead 118. Implantable drug delivery device 320 and implantable drug delivery device 420 are each a specific embodiment of implantable drug delivery device 120.

Implantable drug delivery device 320 includes a drug storage device 322 as a specific embodiment of drug storage device 222 and includes the features of drug storage device 222 discussed above. Drug storage device 322 includes a polymeric matrix 326 made of the electrically sensitive polymer. Drug 225 is embedded in polymeric matrix 326. Polymeric matrix 326 includes a portion configured for tissue contact after implantable drug delivery device 320 is implanted. An electrode 324 is a specific embodiment of electrode 224 and includes the features of electrode 224 as discussed above. Electrode 324 is an electrode or electrode array specifically configured for applying the electric field to polymeric matrix 326.

Implantable drug delivery device 420 includes a drug storage device 422 as a specific embodiment of drug storage device 222 and includes the features of drug storage device 222 discussed above. Drug storage device 422 includes a storage compartment 426 having a wall 423 forming a chamber 427. Drug 225 is contained in chamber 427. At least a portion of wall 423 is made of the electrically sensitive polymer. Wall 423 includes a portion configured for tissue contact after implantable drug delivery device 420 is implanted. In one embodiment, the portion of wall 423 that is configured for tissue contact is made of the electrically sensitive polymer. An electrode 424 is a specific embodiment of electrode 224 and includes the features of electrode 224 as discussed above. Electrode 424 is an electrode or electrode array specifically configured for applying the electric field to the portion of wall 423 made of the electrically sensitive polymer.

It is to be understood that while implantable devices delivering drug to the heart are specifically discussed as examples, the present subject matter is not limited to such devices. A drug delivery device including components similar or identical to drug delivery device 222 and electrode 224, including their various embodiments as discussed above, can be configured for implantation or external use to deliver a drug to any organ of the body. In one embodiment, the drug delivery device is configured as an implantable drug delivery device communicating with implantable CRM device 110 via telemetry, such that lead 118 and lead connector 328 are not needed. In addition to the drug storage device containing the drug and the electrode or electrode array, the external drug delivery patch further includes a telemetry circuit to receive a drug delivery command, such as from implantable CRM device 110 or external system 145, a controller to control the electric field based on the drug delivery command, and a power source such as a rechargeable battery. In a further embodiment, the implantable drug delivery device includes a sensor to sense a physiological signal, and the controller includes a drug delivery signal generator to produce a drug delivery signal based on the sensed physiological signal. In another embodiment, the drug delivery device is configured as an external drug delivery patch for skin attachment. In addition to the drug storage device containing the drug and the electrode or electrode array, the external drug delivery patch further includes a telemetry circuit to receive a drug delivery command, such as from implantable CRM device 110 or external system 145, a controller to control the electric field based on the drug delivery command, and a power source such as a battery. In a further embodiment, the external drug delivery patch includes a sensor to sense a physiological signal, and the controller includes a drug delivery signal generator to produce a drug delivery signal based on the sensed physiological signal.

Figure 5:
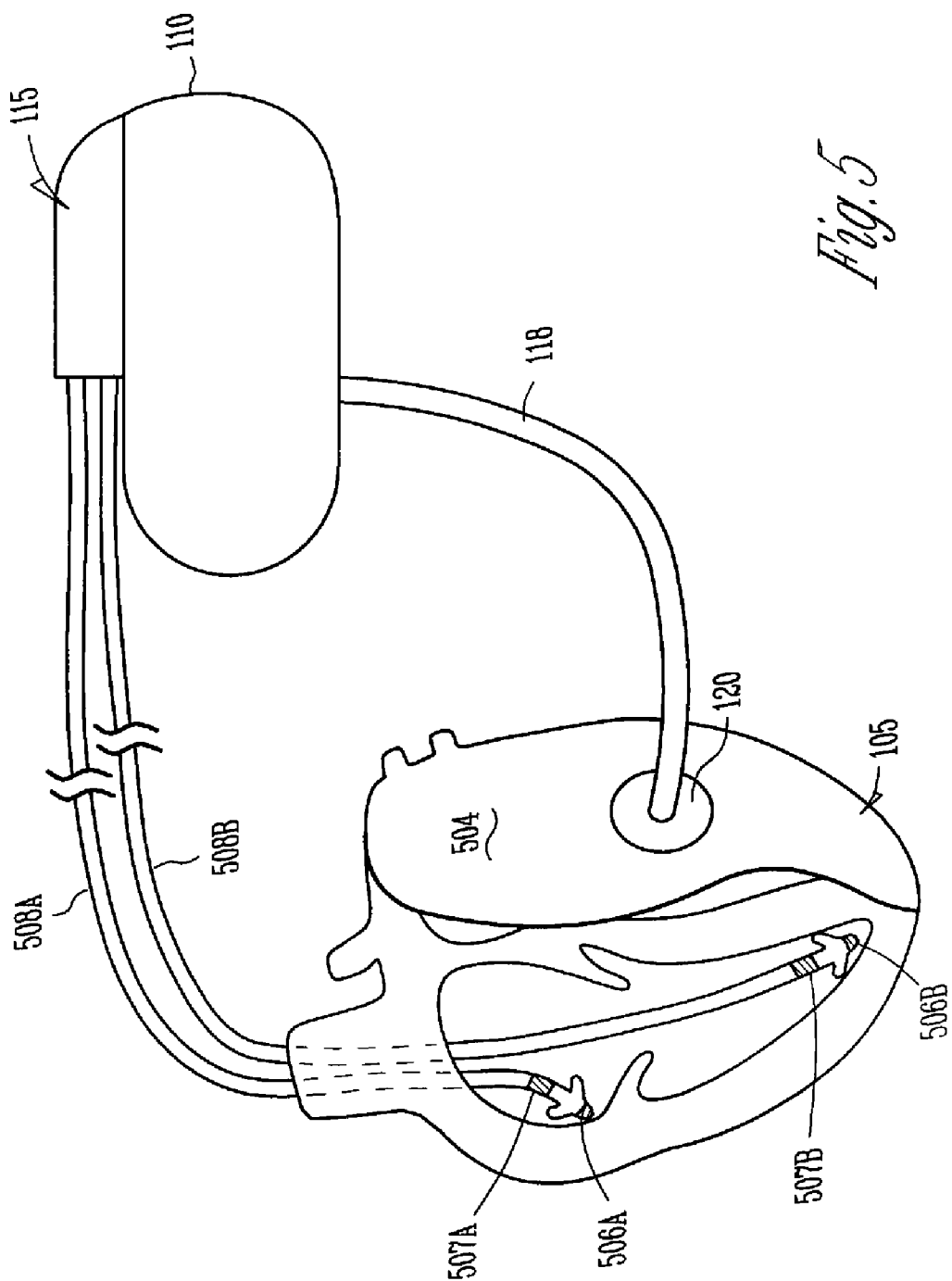
FIG. 5 is an illustration showing a specific embodiment of portions of the CRM system of FIG. 1 and portions of the environment in which the portions of the CRM system is used.

FIG. 5 is an illustration showing a specific embodiment of implantable system 115 and portions of the environment in which implantable system 115 is used. Implantable system 115 includes implantable CRM device 110 coupled to heart 105 via leads 508A and 508B, which are two leads of lead system 108. In this specific embodiment, implantable drug delivery device 120 is configured as an epicardial patch connected to implantable CRM device 110 via lead 118 and is attached to an epicardial surface 504 of heart 105. In one specific example, implantable drug delivery device 120 is used to deliver a drug to an injured area of heart 105. Such injured area results from, for example, myocardial infarction. Implantable drug delivery device 120 is attached onto epicardial surface 504 over at least portions of the injured area to allow localized drug delivery to the injured area and its surrounding tissue.

In the specific embodiment as shown in FIG. 5, lead 508A is an atrial sensing-pacing lead having a tip electrode 506A and a ring electrode 507A for placement in the right atrium, and lead 508B is a ventricular sensing-pacing lead having a tip electrode 506B and a ring electrode 507B for placement in the right ventricle. In another specific embodiment, lead system 108 includes an additional ventricular sensing-pacing lead having one or more electrodes for placement in the left ventricle. In general, lead system 108 includes one or more leads for sensing, pacing, cardioversion, and/or defibrillation. Each lead includes at least one electrode configured for placement in one of the chambers of heart 105 or on epicardial surface 504 of heart 105.

Figure 6:
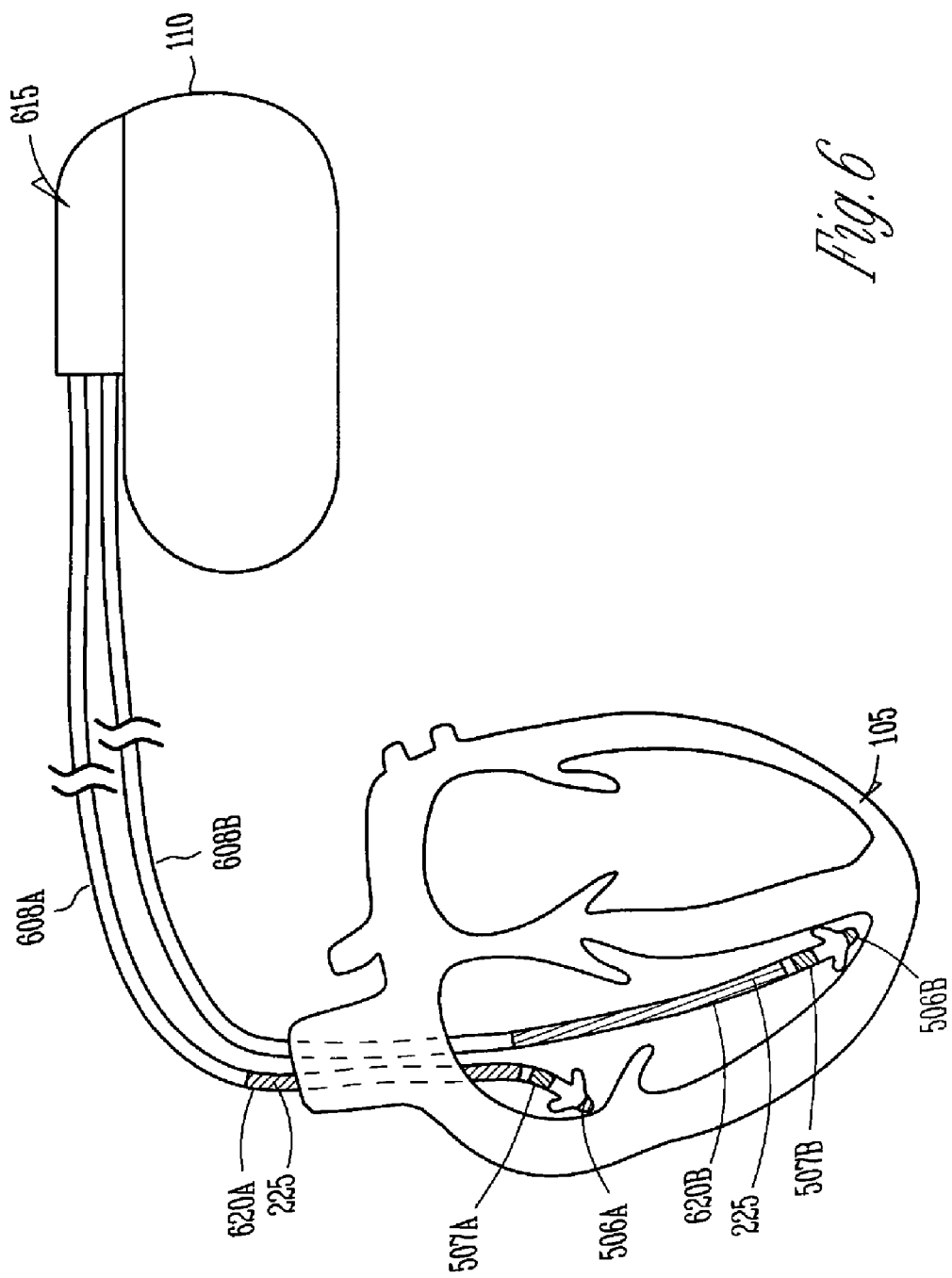
FIG. 6 is an illustration showing one embodiment of an implantable system including leads coated with drug-embedded polymer and portions of the environment in which the implantable system is used.

FIG. 6 is an illustration showing one embodiment of an implantable system 615 and portions of an environment in which implantable system 615 is used. Implantable system 615 is part of a CRM system that also includes external system 145, with which implantable system 615 communicates through telemetry link 140.

Implantable system 615 includes implantable CRM device 110 coupled to heart 105 through leads 608A and 608B. Lead 608A is lead 508A with an additional drug-embedded polymer coating 620A along at least a portion of its length. Lead 608B is lead 508B with an additional drug-embedded polymer coating 620B along at least a portion of its length. Drug-embedded polymer coatings 620A and 620B are each a matrix made of the electrically sensitive polymer and containing drug 225. In one embodiment, drug-embedded polymer coatings 620A and 620B each have a length of at least approximately 2 millimeters and up to the full length of the lead to which the coating is applied. In one embodiment, drug-embedded polymer coatings 620A and 620B each have a thickness of approximately 0.01 to 2 millimeters.

In general, the drug-embedded electrically sensitive polymer can be coated to a portion of portions of any lead used for sensing, pacing, cardioversion, and/or defibrillation. Each coated lead includes at least one electrode configured for placement in one of the chambers of heart 105 or on the epicardial surface of heart 105. In one embodiment, the drug delivery signal or signals are delivered though lead 608A and/or lead 608B to create the electric field that applies to the drug-embedded polymer coating. In another embodiment, the electric field controlling the drug delivery is applied by external means, such as via electrodes attached to the skin. In other embodiments, the drug-embedded electrically sensitive polymer is coated to any implantable device, such as the housing the implantable CRM device 110, a stent, a prosthetic device, or a monitoring device.

Figure 7:
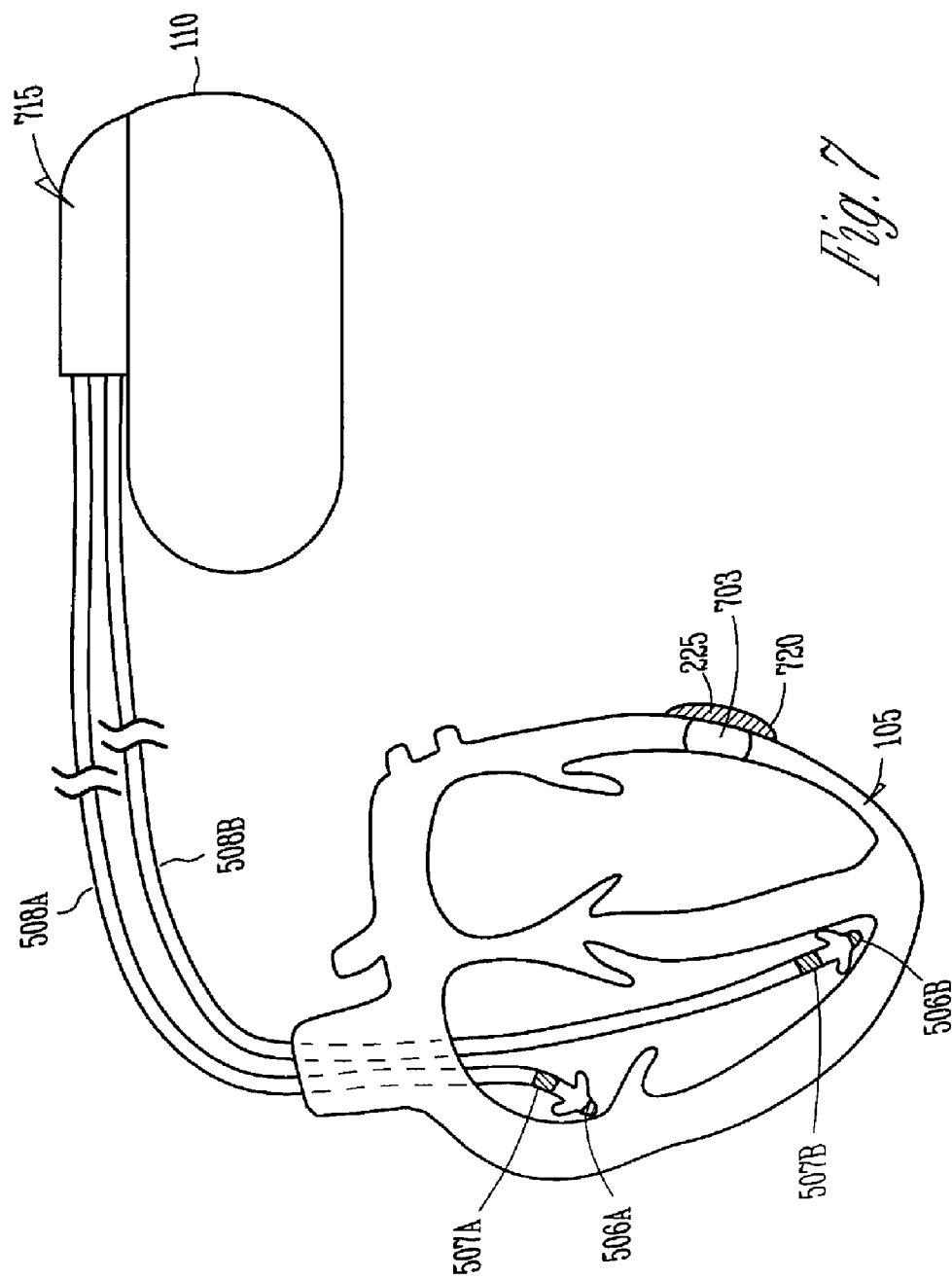
FIG. 7 is an illustration showing one embodiment of an implantable system, a drug-embedded polymeric bulking agent, and portions of the environment in which the implantable system is used.

FIG. 7 is an illustrating showing one embodiment of an implantable system 715 and portions of an environment in which implantable system 715 is used. Implantable system 715 is part of a CRM system that also includes external system 145, with which implantable system 715 communicates through telemetry link 140.

Implantable system 715 includes an article 720 being a bulking agent applied to the myocardium of heart 105 to provide mechanical support to an injured myocardial region 703. The bulking agent is at least partially made of the electrically sensitive polymer. Drug 225 is embedded in the electrically sensitive polymer of the bulking agent. In one embodiment, as illustrated in FIG. 7, the bulking agent is applied to the epicardial surface of heart 105 over injured myocardial region 703. In another embodiment, the bulking agent is injected into the myocardium of heart 105 in or near injured myocardial region 703. In one embodiment, the bulking agent is applied to the endocardial surface of heart 105 under injured myocardial region 703.

In one specific example, injured myocardial region 703 results from myocardial infarction. Combined electrical, drug, and biological therapies are delivered to control the post myocardial infarction remodeling process and repair injured myocardial region 703. The drug is delivered to directly alter the remodeling process and/or to support the biological therapy. Examples of the drug used for such purposes include, but are not limited to, an agent to reduce fibrosis such as matrix metalloprotease (MMP) or small interfering ribonucleic acid (siRNA), an agent to promote fibrosis such as transforming growth factor $\beta 1$ (TGF-$\beta 1$), an angiogenic agent such as vascular endothelial growth factor (VEGF) or fibroblast growth factor (FGF), a cytokine such as FGF or bone morphogenetic protein 4 (BMP-4), an agent to recruit cells for a cell therapy such as stem cell homing factor (SDF-1), and an agent to promote cellular regeneration such as transforming growth factor $\beta 3$ (TGF-$\beta 3$).

Figure 8:
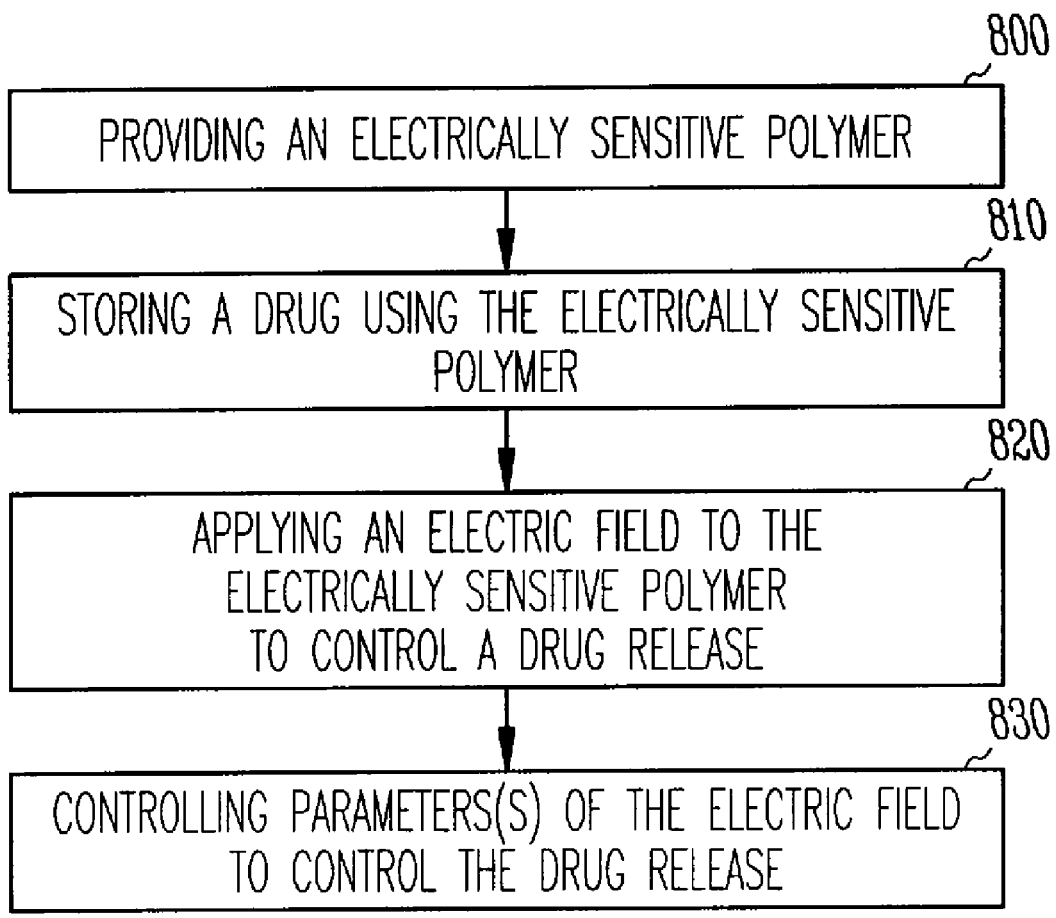
FIG. 8 is a flow chart illustrating a method for delivering a drug using a CRM system.

FIG. 8 is a flow chart illustrating a method for delivering a drug using a CRM system such as any of the CRM systems discussed above. An electrically sensitive polymer is provided at 800. The electrically sensitive polymer has an electrically controllable structure that is a function of an electric field applied onto it. A drug is stored in the electrically sensitive polymer at 810. In one embodiment, the drug is stored in a matrix made of the electrically sensitive polymer. In another embodiment, the drug is stored in a container that is at least partially made of the electrically sensitive polymer.

An electric field is applied to the electrically sensitive polymer containing the drug for controlling the release of the drug at 820. In one embodiment, this includes delivering a plurality of electrical signals to an electrode array of a plurality of electrodes. The electrodes are each configured to apply the electric field to a portion of the electrically sensitive polymer. Thus, each electrical signal controls the electric field strength in a portion of the electrically sensitive polymer. This allows control of spatial distribution of electric field strength throughout the electrically sensitive polymer.

The release of the drug is temporally and quantitatively controlled by controlling one or more parameters of the electric field at 830, such as the amplitude and frequency of the electric field and the timing of application of the electric field. The structure of the electrically sensitive polymer, and hence the drug release rate, are controlled by the amplitude of the electric field. In one embodiment, the porosity (size of the pores) of the electrically sensitive polymer is controlled by controlling the one or more parameters of the electric field. In one specific embodiment, the amplitude of the electric field is controlled by switching between at least a first amplitude and a second amplitude. The first amplitude provides for a substantially porous state of the electrically sensitive polymer. The second amplitude provides for a substantially non-porous state of the electrically sensitive polymer. In another embodiment, the binding affinity of the electrically sensitive polymer is controlled by controlling the one or more parameters of the electric field. In one specific embodiment, the amplitude of the electric field is controlled by switching between at least a first amplitude and a second amplitude. The first amplitude provides the electrically sensitive polymer with a state of low binding affinity. The second amplitude provides the electrically sensitive polymer with a state of high binding affinity. In one embodiment, the electric field is a direct current (dc) electric field. In another embodiment, the electric filed is a low frequency alternating current (ac) electric field. The low frequency ac electric field causes periodic change in the structure of the electrically sensitive polymer, thus providing a continuous release of the drug at a slow rate. The timing of the application of the electric field is controlled by following a predetermined schedule or a drug delivery command. In one embodiment, a pulsed electric field is applied. The pulsed electric field has a duty cycle with an on-phase and an off-phase. The on-phase is associated with the first amplitude providing for the substantially porous state or the state of low binding affinity. The off-phase is associated with the second amplitude providing for the substantially non-porous state or the state of high binding affinity. In one specific embodiment, the timing of the application of the electric field is controlled by switching between the on-phase and the off-phase according to a predetermined schedule, such as on a periodic basis. In another embodiment, the timing of the application of the electric field is controlled by switching to the on-phase in response to the command. In one embodiment, a signal indicative of a predetermined event is sensed, and the command is issued when the predetermined event is detected. In another embodiment, the command is issued by a physician or other caregiver.

It is to be understood that the above detailed description is intended to be illustrative, and not restrictive. Other embodiments, including any possible permutation of the system components discussed in this document, will be apparent to those of skill in the art upon reading and understanding the above description. The scope of the invention should, therefore, be determined with reference to the appended claims, along with the full scope of equivalents to which such claims are entitled.

What is claimed is:

1. A system, comprising:
    an implantable drug delivery device including:
        a drug storage device including a polymeric matrix made of an electrically sensitive polymer having a structure that is electrically controllable by applying an electric field on the electrically sensitive polymer, the structure including an electrically controllable porosity or an electrically controllable binding affinity;
        a drug embedded in the polymeric matrix; and
        a plurality of electrodes, coupled to the drug storage device, the plurality of electrodes to apply a plurality of electric fields each on a portion of the electrically sensitive polymer and having an individually controllable amplitude; and
    an implantable lead including a proximal end including a lead connector providing for a detachable connection to an implantable cardiac rhythm management (CRM) device and a distal end at the implantable drug delivery device, the implantable lead providing for electrical connections between the implantable CRM device and the plurality of electrodes to allow a plurality of drug delivery signals controlling the application of the plurality of electric fields to be delivered from the implantable CRM device to the plurality of electrodes.

2. The system of claim 1, wherein the electrically sensitive polymer has the electrically controllable porosity.

3. The system of claim 2, wherein the electrically sensitive polymer is configured to enter a substantially porous state upon application of the electrical field at a first amplitude and a substantially non-porous state upon application of the electrical field at a second amplitude.

4. The system of claim 2, wherein the electrically sensitive polymer is configured to enter a substantially porous state upon application of the electrical field and a substantially non-porous state upon removal of the electrical field.

5. The system of claim 1, wherein the electrically sensitive polymer has the electrically controllable binding affinity.

6. The system of claim 5, wherein the electrically sensitive polymer is configured to enter a state of low binding affinity upon application of the electrical field at a first amplitude and a state of high binding affinity upon application of the electrical field at a second amplitude.

7. The system of claim 5, wherein the electrically sensitive polymer is configured to enter a state of low binding affinity upon application of the electrical field and a state of high binding affinity upon removal of the electrical field.

8. The system of claim 1, wherein the implantable drug delivery device comprises a patch configured for epicardial attachment.

9. The system of claim 1, wherein the implantable drug delivery device is configured for intracardiac placement.

10. The system of claim 1, wherein the implantable drug delivery device is configured for intravascular placement.

11. The system of claim 1, wherein the drug comprises at least one biological agent.

12. The system of claim 1, wherein the drug comprises one or more of:
    an agent treating arrhythmia;
    an agent treating heart failure;
    an agent treating diastolic dysfunction;
    an agent providing ischemia protection;
    an agent altering fibrosis;
    an angiogenic agent;
    a cytokine;
    an agent recruiting cells for a cell therapy; and
    an agent promoting cellular regeneration.

13. The system of claim 1, comprising the implantable CRM device, and wherein the implantable CRM device includes a drug delivery controller to produce the plurality of drug delivery signals and deliver the plurality of drug delivery signals to the plurality of electrodes.

14. The system of claim 13, wherein the implantable CRM device includes an implant controller, coupled to the drug delivery controller, to receive an external command transmitted to the implantable CRM device, and wherein the drug delivery controller is adapted to produce the plurality of drug delivery signals based on the external command.

15. The system of claim 14, further comprising:
    an external device communicatively coupled to the implantable CRM device via telemetry;
    a remote device including a user input configured to allow a user to enter the external command; and
    a network configured to provide bi-directional communication between the external device and the remote device.

16. The system of claim 13, wherein the drug delivery controller is adapted to produce the plurality of drug delivery signals to control an amplitude of each electric field of the plurality of electric fields.

17. The system of claim 13, wherein the drug delivery controller is adapted to produce the plurality of drug delivery signals to control a timing of the application of each electric field of the plurality of electric fields.

18. The system of claim 13, wherein the drug delivery controller is adapted to produce the plurality of drug delivery signals to control a duty cycle of each electric field of the plurality of electric fields.

19. The system of claim 13, further comprising a sensor to sense a signal indicative of an effect of drug delivery, and wherein the drug delivery controller is adapted to produce the one or more drug delivery signals by using the signal indicative of the effect of drug delivery as a feedback control signal.

* * * * *

UNITED STATES PATENT AND TRADEMARK OFFICE
CERTIFICATE OF CORRECTION

PATENT NO. : 7,621,906 B2
APPLICATION NO. : 10/925508
DATED : November 24, 2009
INVENTOR(S) : Pastore et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 466 days.

Signed and Sealed this

Fourteenth Day of December, 2010

David J. Kappos
*Director of the United States Patent and Trademark Office*